United States Patent
Jacobsen et al.

(10) Patent No.: US 6,302,870 B1
(45) Date of Patent: Oct. 16, 2001

(54) APPARATUS FOR INJECTING FLUIDS INTO THE WALLS OF BLOOD VESSELS, BODY CAVITIES, AND THE LIKE

(75) Inventors: Stephen C. Jacobsen; Clark C. Davis, both of Salt Lake City, UT (US)

(73) Assignee: Precision Vascular Systems, Inc., Salt Lake City, UT (US)

( * ) Notice: Subject to any disclaimer, the term of this patent is extended or adjusted under 35 U.S.C. 154(b) by 0 days.

(21) Appl. No.: 09/302,340

(22) Filed: Apr. 29, 1999

(51) Int. Cl.[7] .................................................. A61M 5/32
(52) U.S. Cl. ................. 604/272; 604/170.03; 604/164.09
(58) Field of Search ........................... 604/27, 48, 93, 604/96, 104, 105, 106, 107, 108, 109, 117, 158, 164.01, 164.09, 166, 170.01, 170.03, 192, 198, 272, 523; 606/191, 192, 194

(56) References Cited

U.S. PATENT DOCUMENTS

| | | |
|---|---|---|
| 5,112,305 | 5/1992 | Barath et al. . |
| 5,354,271 * | 10/1994 | Voda ........................................ 604/49 |
| 5,354,279 | 10/1994 | Höfling . |
| 5,364,356 | 11/1994 | Höfling . |
| 5,419,777 * | 5/1995 | Hofling ................................ 604/264 |
| 5,536,250 * | 7/1996 | Klein et al. ............................ 604/96 |
| 5,591,159 * | 1/1997 | Taheri .................................... 606/15 |
| 5,599,306 * | 2/1997 | Klein et al. ............................ 604/96 |
| 5,681,281 | 10/1997 | Vigil et al. . |
| 5,693,029 * | 12/1997 | Leonhardt ........................... 604/264 |
| 6,102,887 * | 8/2000 | Altman . |

* cited by examiner

Primary Examiner—Anhtuan T. Nguyen
Assistant Examiner—Catherine Serke
(74) Attorney, Agent, or Firm—McDermott, Will & Emery

(57) ABSTRACT

Apparatus for injecting fluids into the walls of blood vessels, body cavities, and the like, includes a plurality of laterally flexible needles disposed in a catheter for exit either out the distal end of the catheter or the catheter or through corresponding side openings in the catheter. In the latter case, the terminal ends of the needles would be curved laterally, with each terminal end being positioned in a respective side opening so that when the needles were moved forwardly in the catheter, the terminal ends of the needles would move laterally out the respective openings to pierce a vessel or cavity wall adjacent to which the catheter was positioned. Hilts positioned near the terminal ends of the needles serve to control the depth of penetration of the needles.

20 Claims, 3 Drawing Sheets

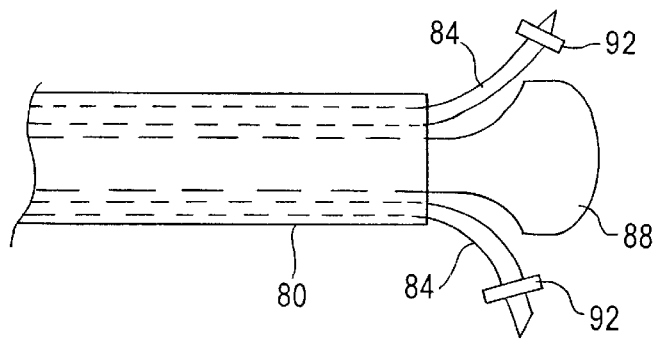
FIG. 4
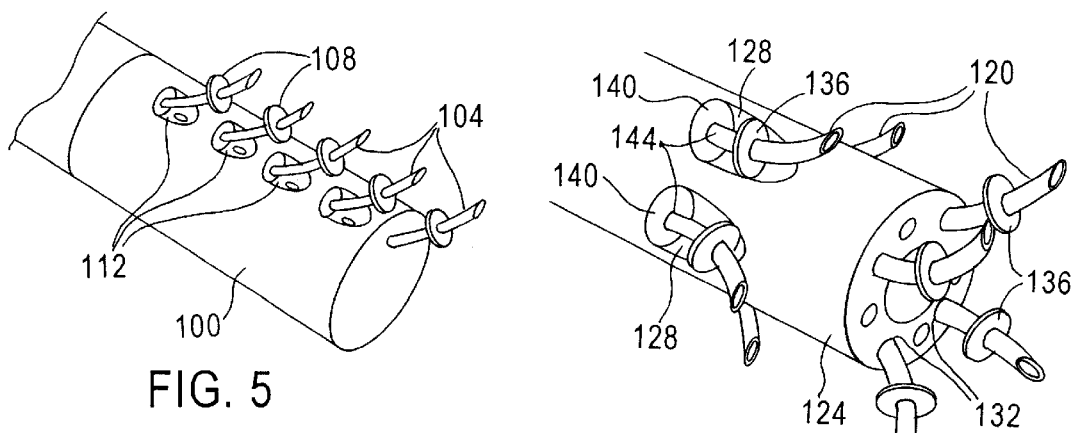
FIG. 5
FIG. 6
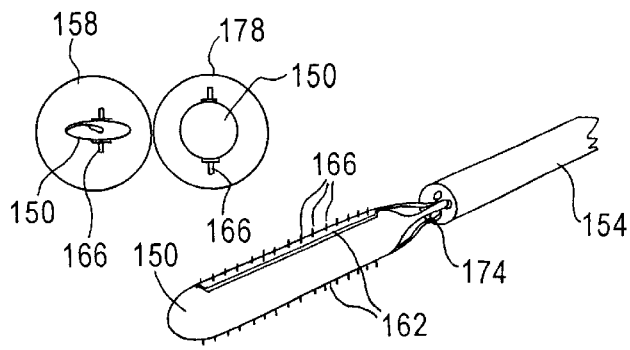
FIG. 7A
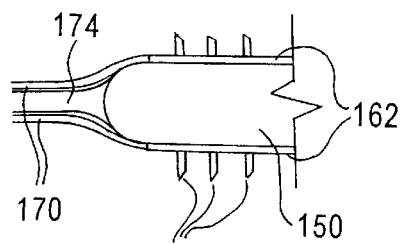
FIG. 7B

APPARATUS FOR INJECTING FLUIDS INTO THE WALLS OF BLOOD VESSELS, BODY CAVITIES, AND THE LIKE

BACKGROUND OF THE INVENTION

1. Field of the Invention

This invention relates to invasive medical devices for injecting medications and therapeutic agents into the walls of blood vessels, body cavities, ducts, organs, tumors and the like. More particularly, the present invention relates to devices for concentrating the delivery of such medications and agents to the walls of the blood vessels, cavities and ducts.

2. State of the Art

Various vascular diseases involving vessel walls, such as arterial sclerosis, occlusive lesions, aneurysm or other weakening of the vessel wall, etc., may benefit from the application of medications directly to the affected area of the vessel wall. This may be done systemically by injecting medication into the vessel and then allowing the blood to carry the medication to the affected area. The problem with this approach is that high dosages of medication are required to ensure that some small portion reaches the affected area, and the high dosage may be harmful to other organs or body parts. Also, systemic application is generally not effective and quite expensive.

Another approach to treating diseases of vessel walls is to place a block before and after the affected area and then inject medications into that portion of the vessel between the two blocks. The problem with this approach is that blood flow is stopped for a certain amount of time and this, in itself, is dangerous; also, may not be able to stop the flow long enough for uptake of the medications.

Another prior art approach is to thread a catheter through the blood vessel to the affected area and then either supply the medication through the catheter to the affected area or supply the medication through a needle which itself is threaded through the catheter, pierce the vessel wall with the needle, and then supply the medication (see U.S. Pat. No. 5,354,279). The problem with simply supplying the medication via the catheter is that much of the medication is carried away in the blood and may adversely affect other organs.

An additional prior art approach to supplying medication to a vessel wall involves the use of an inflatable sleeve positioned adjacent the affected area, where the sleeve includes an annular cavity holding the medication. When the sleeve is inflated to expand outwardly, the medication held in the cavity is placed into contact with the vessel walls and released thereinto. The problem with this approach is that the blood vessel again is blocked for a time and thus a gradual therapeutic regimen is not possible.

Other approaches to delivering medication to vessel walls are disclosed in U.S. Pat. Nos. 5,681,281, 5,364,356, and 5,112,305.

OBJECTS AND SUMMARY OF THE INVENTION

It is therefore an object of the present invention to provide a device for injecting medication, therapeutic agents, and the like efficiently and effectively into a blood vessel wall, body cavity wall, duct wall, etc.

It is also an object of the invention to provide such a device which is non-occlusive and substantially non-inhibiting of blood flow.

It is a further object of the invention to provide such a device which may be easily deployed through the vascular system and other body cavities or ducts to desired target locations for delivering the medication, therapeutic agents, and the like.

It is an additional object of the invention to provide such a device, in accordance with one aspect thereof, in which the vessel or cavity wall may be penetrated and the degree of penetration may be controlled.

The above and other objects are realized in one illustrative embodiment of the invention which includes a plurality of laterally flexible needles disposed in a catheter for exit either out the distal end of the catheter or through corresponding side openings in the catheter. In the latter case, the terminal ends of the needles would be curved laterally, with each terminal end being positioned in a respective side opening so that when the needles were moved forwardly in the catheter, the terminal ends of the needles would move laterally out of the respective openings to pierce a vessel, cavity or duct wall adjacent to which the catheter was positioned. In the former case, the terminal ends of the needles would be curved to extend radially so that upon exit from the distal end of the catheter, the terminal ends of the needles would move radially to contact and pierce a vessel or cavity wall.

Upon piercing the vessel or cavity wall, medication would be supplied to the needles for delivery to the vessel, cavity or duct wall. Hilts positioned near the terminal ends of the needles serve to control the depth of penetration of the needles.

BRIEF DESCRIPTION OF THE DRAWINGS

The above and other objects, features and advantages of the invention will become apparent from a consideration of the following detailed description presented in connection with the accompanying drawings in which:

FIG. 4 is a side, elevational view of another embodiment of the invention in which needles are deflected radially outwardly by a guide;

FIG. 5 is a perspective, fragmented view of a further embodiment of the invention in which a plurality of needles are carried by a catheter, with the ends of the needles nesting in a linear array of pockets until use;

FIG. 6 is a fragmented, perspective view of still another embodiment of the invention in which a plurality of needles are carried by a catheter, with the ends of the needles nesting in circumferentially disposed pockets until use;

FIGS. 7A and 7B show respectively a perspective view and a fragmented, side cross-sectional view of a balloon actuated needle injection system made in accordance with the present invention;

DETAILED DESCRIPTION OF THE PREFERRED EMBODIMENT

Figure 1:
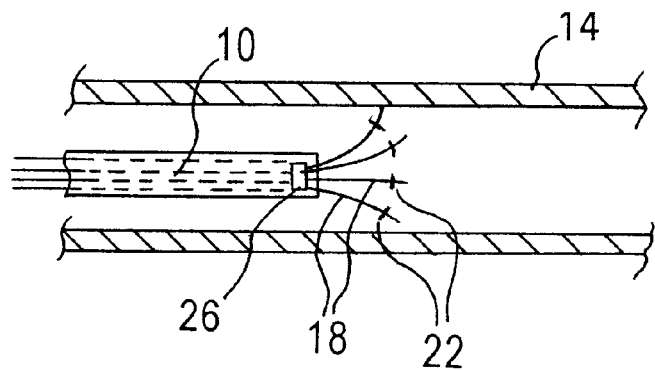
FIG. 1 is a side, partially cross-sectional view of one embodiment of the present invention in which radially projecting needles are used for delivery of medication to vessel or cavity walls.

Referring to FIG. 1, there is shown a side, fragmented, partially cross-sectional view of one embodiment of a device for delivering medication to the walls of a vessel, duct or body cavity. Here, the distal end of a catheter 10 is shown disposed within a blood vessel 14. Disposed in the catheter 10 are a plurality of tiny hollow needles 18 whose terminal ends are preshaped to curve radially outwardly when unconstrained by the catheter 10. Thus, when pushed out of the distal end of the catheter 10, the terminal ends of the needles 18 curve radially toward the walls of the blood vessel 14 to pierce the walls. Medication may then be supplied through the needles 18 into the vessel walls to treat the vessel wall in a circumferential manner.

Hilts 22 are provided near the terminal ends of the needles 18 to prevent piercing the walls of the blood vessel 14 beyond a certain distance. In particular, the needles penetrate the vessel wall until the hilt makes contact therewith to stop further penetration. The hilts 22 may be selectively positioned at the terminal ends of the needles 18 to effectively control the depth of penetration of the needles. Advantageously, the needles may be made of stainless steel, and the catheter of various plastics.

A radiopaque marker 26 may be provided on the distal end of the catheter 10 to allow tracking the position of the end of the catheter in the body (by radioscopy), and thus, the position or location at which the needles exit the catheter.

Figure 2:
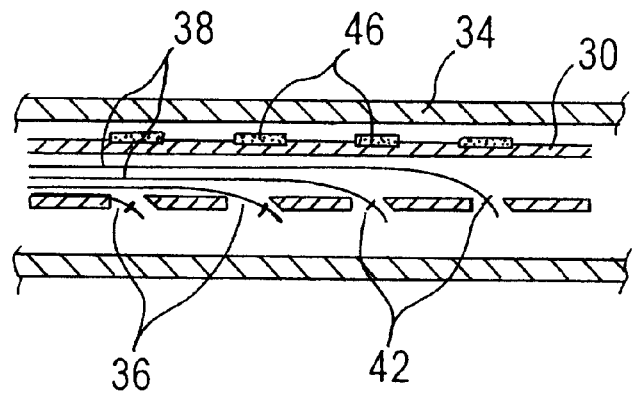
FIG. 2 is a side, cross-sectional view of another embodiment of the present invention in which a plurality of needles, exiting through a linear array of openings in a catheter, are used to inject medication into vessel or cavity walls.

FIG. 2 is an alternative embodiment of a needle injection device made in accordance with the present invention. Here, a catheter 30 is shown disposed within a blood vessel 34. The catheter 30 includes a plurality of openings 36 generally arrayed in a line on one side of the catheter, and in which are positioned the terminal ends of hollow needles 38. The needles would be placed in the catheter 30 with their terminal ends positioned in the openings 36, and then the catheter would be threaded into the blood vessel 34 to the target location.

The terminal ends of the needles 38 are preformed with a curve so that when the catheter 30 is moved adjacent to the target location, the needles may be moved forwardly in the catheter, causing the needles to exit the openings 36 and move laterally into contact and pierce the walls of the blood vessel 34. The terminal ends of the needles 38 also include hilts 42 to prevent the needles 38 from piercing the vessel wall greater than a certain distance.

To facilitate rotational positioning of the catheter 30 (so that the openings 36 are positioned adjacent the area to be treated), the catheter may be constructed with a proximal section formed to be torsionally stiff (e.g. stainless steel) and a distal section formed to be torsionally stiff yet laterally flexible (e.g. nickel-titanium alloy including cuts to predetermine the flexibility). See co-pending U.S. patent application, Ser. No. 08/653,289, filed May 24, 1996. Radiopaque markers 46 could also be provided as described for the FIG. 1 embodiment. After the needles 98 are in place in the vessel wall, medication would be supplied to the needles for injection into the vessel wall as desired.

Figure 3:
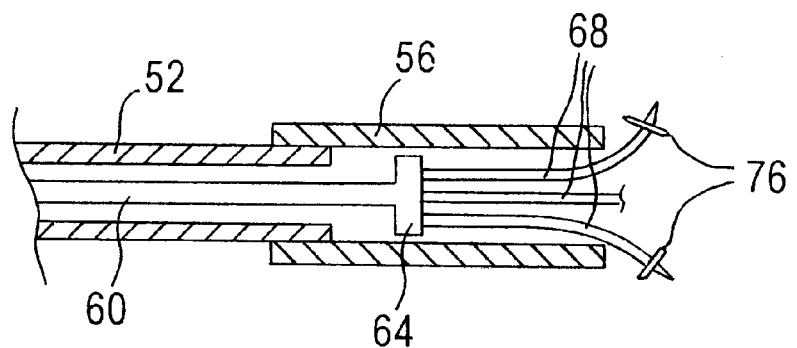
FIG. 3 is a side, elevational, cross-sectional view of an embodiment of the present invention which includes a single supply tube with multiple terminal needles for supplying medication, all carried in a catheter.

FIG. 3 shows a fragmented, side, cross-sectional view of another embodiment of the invention, which includes a primary catheter section 52 on the distal end of which is a secondary catheter section 56. A single hollow needle or tube 60 is disposed in the primary catheter section 52, and includes a manifold 64 formed on the distal end of the tube. Extending forwardly from the manifold 64 are a plurality of needles 68 and 72, formed to curve radially outwardly at their terminal ends when unconstrained. Thus, when the tube is withdrawn so that the manifold 64 abuts against the end of the primary catheter section 52, the ends of the needles 68 and 72 are withdrawn into the secondary catheter section 56. When the tube 60 is moved forwardly, the ends of the needles 68 and 72 emerge from the secondary catheter section 56 and curve radially outwardly to pierce the walls of a blood vessel, duct or body cavity into which the device has been inserted. Hilts 76 disposed near the pointed ends of the needles 68 and 72, prevent penetration of the needles beyond a certain distance, as described earlier.

FIG. 4 is a side, elevational view of another embodiment of the invention somewhat similar to the embodiment of FIG. 1. In FIG. 4, a distal end of a catheter 80 is shown, with a plurality of small hollow needles 84 disposed in the catheter. Also disposed in the catheter 80 is a deflection guide 88 which is enlarged on its distal end so that when the needles 84 are pushed forwardly in the catheter 80, the ends of the needles are deflected radially outwardly as shown to penetrate the walls of a blood vessel, duct or body cavity. Hilts 92 are formed near the tips of the needles to limit the depth of penetration of the needles in the body cavity wall.

Of course, once the needles have been deployed to penetrate the body cavity walls, medication would be supplied through the needles and into the walls for the desired treatment.

FIG. 5 is a perspective, fragmented view of a further embodiment of the invention, and shows a distal end of a catheter 100 in which are disposed a plurality of small needles 104. Hilts 108 are disposed near the ends of the needles 104 as previously described. Formed in a side wall of the catheter 100 are a plurality of pockets or recesses 112 into which the ends of the needles 104, along with the respective hilts 108 can nest when the needles are withdrawn. When the needles 104 are pushed forwardly, the ends are preformed to curve and move radially outwardly to penetrate the wall of a blood vessel, duct or body cavity, as before described. Note that the pockets 112 and needles 104 are arranged generally in a line, similar to the configuration of FIG. 2.

FIG. 6 is a fragmented, perspective view of still another embodiment of the invention in which a plurality of needles 120 are carried by a catheter 124, with some of the needles 120 positioned radially about the catheter 124 to nest in respective pockets or recesses 128, and with other needles positioned to extend out the distal end of the catheter through openings 132. The openings 132 allow for the needles 120 to project therethrough, but are too small for hilts 136 formed near the ends of the needles to slide through the openings. Thus, when the needles 120 which project out the end of the catheter 124 are withdrawn, the hilts 136 serve as a stop for withdrawing the needles too far. Similarly, the needles disposed radially about the side of the catheter 124 and which nest in pockets 128, also are limited as to how far they may be withdrawn by the hilts 136 contacting rear walls 140 formed in the recesses 128. The needles 120 project through openings 144 in the rear walls 140 and can slide readily therein, but the hilts 136 are too large to move through the openings.

The needles 120 are preformed to curve radially outwardly when the needles are moved forwardly in the catheter 124 so that the needles may penetrate walls of blood vessels, ducts, or body cavities into which the catheter has been threaded.

FIGS. 7A and 7B show respectively a perspective view and a fragmented, side cross-sectional view of a balloon actuated needle injection system made in accordance with the present invention. The system includes an elongate balloon 150 which is initially disposed in a catheter 154 in a deflated condition, as indicated in the end, cross-sectional view at 158.

Disposed on opposite sides of the balloon 150 are a pair of hollow rails 162 in which are disposed a plurality of laterally extending hollow needles 166 as best seen in FIG. 7B. The hollows in the needles 166 are in communication with the respective hollows in the rails 162 so that medication supplied to the hollow of the rails will flow through and out the needles. A pair of supply tubes 170 are coupled to respective ones of the hollow rails 162, again as best seen in FIG. 7B.

A tube 174 is coupled to a rear end of the balloon 150 to supply air or other gas to inflate the balloon and thereby force the rails laterally outwardly to cause the needles 166 to pierce adjacent walls of a blood vessel, duct or other body cavity. An end view of an inflated balloon is shown at 178.

The tubes 170 coupled to the hollow rails 162 extend in the catheter 154 on either side of the tube 174 which is coupled to the rear end of the balloon 150. Advantageously, the tubes 174 are longitudinally stiff to allow pushing the rails 162 forwardly in the catheter 154 to carry along the balloon 150 until the balloon and rails reach the desired target location. The device is inserted with the needle rails 162 withdrawn up inside a catheter to protect the vessel walls from abrasion.

Figure 7C:
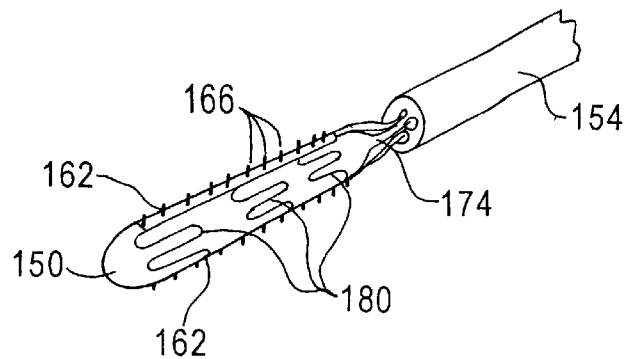
FIG. 7C depicts the balloon actuated needle injection system of FIGS. 7A and 7B wherein the rails are supported by one or more stent-like biasing structures.

The rails 162 may be affixed to the balloon 150 for support, as shown in FIGS. 7A and 7B. Alternatively, they may be supported by one or more stent-like biasing structures 180, shown in FIG. 7C. As is well known to those skilled in the art, a stent is a device used to provide support for tubular structures or passageways such as blood vessels, etc. Like a stent, the biasing structures 180 are spring-like coils which surround the balloon 150 to force the rails 162 outward when not constrained within the catheter 154. Unlike stents, however, the biasing structures 180 have elastic memory which causes them to return to a small size for retraction through the catheter.

Figure 8A:
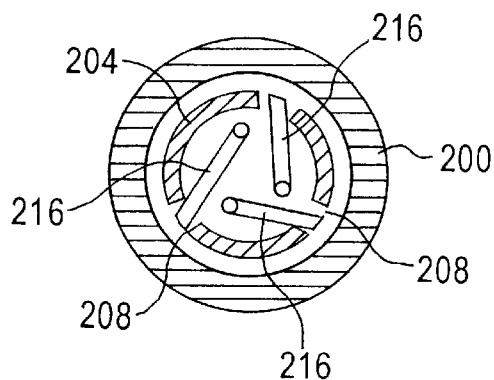
FIGS. 8A and 8B show respectively an end cross-sectional view and a side cross-sectional view of an embodiment of the invention in which radially projecting needles are moved into position by rotational action.
Figure 8B:
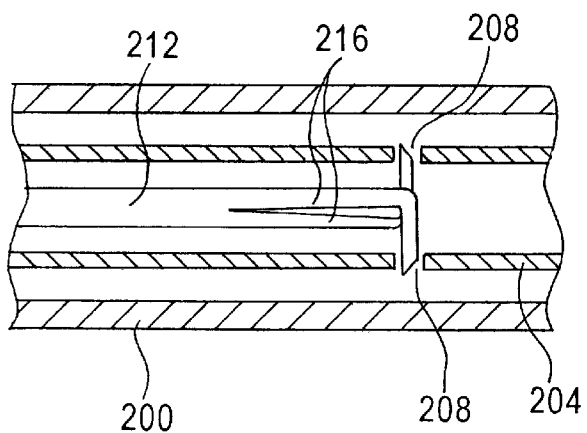

FIG. 8A provides a cross-sectional view of another embodiment of the present invention, and FIG. 8B is a side, cross-sectional view. Shown is a wall 200 of a blood vessel (or other body cavity). A catheter 204 is disposed in the blood vessel, and includes three openings 208 circumferentially spaced apart about the catheter as shown. Disposed in the lumen of the catheter is a supply tube 212 (FIG. 8B) having three branching needles 216 at its terminal or distal end. The needles 216 initially branch forwardly and then are curved radially outwardly so that the sharp ends of each of the needles resides in a respective one of the openings 208 of the catheter 204.

In use, after the catheter 204, with supply tube 212, is in position in the blood vessel, the supply tube 212 is rotated as indicated in FIGS. 8A and 8B and this causes the curved ends of the needles 216 to move generally radially outwardly through the openings 208 to pierce the vessel wall 200. Medication may then be supplied via the supply tube 212 and through the needles 216, into the vessel wall 200. In this manner, after positioning the catheter and supply tube at a target location, a simple rotational movement causes extension of the needles 216 to pierce the vessel wall to allow application of medication.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. An apparatus configured for injecting medication into a wall of a body passageway, comprising:
    a catheter having a lumen and distal end section with a plurality of openings formed generally on one side of the distal end section; and
    a plurality of laterally flexible needles disposed in the lumen of the catheter, with a terminal end of each needle positioned in a respective opening such that movement of the needles forwardly in the catheter causes the terminal ends of the needles to emerge laterally from the openings to pierce an adjacent body duct wall, the needles further including laterally extending hilts formed near the terminal ends thereof to prevent each respective needle from piercing a duct wall beyond the distance from each hilt to the terminal end of the respective needle.

2. The apparatus as in claim 1 wherein the terminal ends of the needles are curved laterally in the direction of the respective openings.

3. The apparatus as in claim 1 wherein said catheter is constructed with a relatively torsionally stiff proximal section, and a relatively torsionally stiff yet laterally flexible distal section.

4. The apparatus as in claim 1 further including one or more radiopaque markers disposed adjacent one or more of said openings.

5. An apparatus configured for injecting medication into a wall of a blood vessel or duct, comprising:
    a catheter having a lumen and a distal end, configured for threading into a body passageway to a treatment location;
    at least one laterally flexible needle disposed in the lumen of the catheter, with a terminal end of each needle biased to curve radially outwardly towards the wall of the body passageway and to pierce said wall when the needle is moved out of the distal end of the catheter; and
    A laterally extending hilt formed on each needle near the terminal end thereof, configured to prevent each respective needle from piercing the wall beyond the distance from each hilt to the terminal end of each needle.

6. The apparatus as in claim 5 further including a radiopaque marker disposed at or near the distal end of the catheter.

7. An apparatus configured for injecting medication into a blood vessel, body duct or body cavity wall, comprising:
    a catheter having a plurality of lumens, configured for threading into a blood vessel, body duct or body cavity, each lumen being curved at a distal end thereof generally radially outwardly toward the vessel, duct or cavity wall;
    a plurality of laterally flexible needles, each disposed in a respective lumen such that movement of the needles forwardly in the catheter causes a terminal end of each needle to emerge laterally from the terminal end of each of the lumens so as to enable it to pierce an adjacent wall of the vessel, duct or cavity; and laterally extending hilts formed on the needles near the terminal ends thereof to prevent each respective needle from piercing the vessel, duct or cavity wall beyond the distance from each hilt to the terminal end of the respective needle.

8. The apparatus as in claim 7 further including means formed at the terminal ends of the lumens for deflecting and guiding the terminal ends of the respective needles laterally outwardly from the catheter.

9. Apparatus for injecting medication into a wall of a body passageway, comprising:

a catheter having a lumen with a first interior diameter, said catheter having a distal end section with a second interior diameter greater than the first diameter, for threading into a body passageway to a treatment location;

a hollow tube disposable in the lumen with the first interior diameter; and a manifold disposed in the distal end section of the catheter and coupled to a terminal end of the tube, and having a plurality of laterally flexible needles extending forwardly from the manifold and biased to curve radially outwardly towards the passageway walls and pierce said walls when the hollow tube is moved forwardly in the catheter so that the plurality of needles are moved out of the distal end section of the catheter.

10. The apparatus as in claim 9 further including hilts formed on the plurality of laterally flexible needles near the terminal ends thereof to prevent each respective needle from piercing the passageway wall beyond the distance from each hilt to the terminal end of the respective needle.

11. An apparatus configured for injecting medication into a wall of a body passageway, comprising:

a catheter having at least one lumen and a distal end configured for threading into a body passageway to a treatment location, the exterior of the catheter formed with at least one pocket in communication with the lumen;

at least one needle disposed in the lumen, with a distal end of the needle extending from the lumen into the exterior pocket to nest therein until the needle is pushed forwardly in the catheter to force the distal end out of the pocket to curve radially outwardly to penetrate the passageway wall; and a laterally extending hilt formed on each needle near the distal end thereof configured to nest in the pocket until the needle is pushed forwardly in the catheter to force the distal end and hilt out of the pocket, the hilt preventing penetration of the needle beyond the distance from the hilt to the terminal end of the needle.

12. The apparatus as in claim 11 wherein the exterior of the catheter comprises a plurality of said pockets arranged generally on one side of the catheter near the distal end.

13. The apparatus as in claim 11 wherein the exterior of the catheter is formed with a plurality of pockets arranged generally circumferentially about the catheter near the distal end.

14. Apparatus for injecting medication into a wall of a body passageway, comprising:

a catheter having at least one lumen and a distal end for threading into a body passageway to a treatment location;

an elongate inflatable balloon for disposition in the lumen of the catheter near the distal end;

at least one elongate tubular rail disposed generally on one side of the balloon and in parallel therewith, for receiving medication, said tubular rail including a plurality of needles projecting laterally outwardly therefrom;

balloon inflating means coupled to the balloon through the lumen, for selectively inflating the balloon when the balloon is pushed out the distal end of the catheter to force the tubular rail outwardly to cause the needles to pierce any adjacent walls; and medication supplying means coupled to the tubular rail through the lumen, for supplying medication to the tubular rail and thus to and out the needles.

15. The apparatus as in claim 14 wherein said balloon inflating means comprises a substantially longitudinally rigid and laterally flexible tube coupled at one end to the balloon and extending rearwardly therefrom through the body passageway.

16. The apparatus as in claim 14 further including a second tubular rail disposed on the opposite side of the balloon from the at least one tubular rail, and generally in parallel therewith, for receiving medication, said second tubular rail including a plurality of needles projecting laterally outwardly therefrom.

17. The apparatus as in claim 16 wherein said medication supplying means comprises a pair of tubes each coupled to a respective tubular rail for supplying medication thereto.

18. The apparatus as in claim 14 wherein said at least one tubular rail is attached to and supported by said balloon.

19. The apparatus as in claim 14, further comprising at least one stent-like structure connected to said at least one tubular rail to provide support thereto.

20. Apparatus for injecting medication into a wall of a body passageway, comprising:

a catheter having at least one lumen and a distal end for threading into a body passageway to a treatment location, said catheter including at least one opening in the side, near the distal end; and a tube disposable in the lumen of the catheter and having a distal end section with a tip, said end section curving laterally so that the tip resides in the opening in the catheter, and so that when the tube is rotated in one direction, the tip is forced out of the opening to pierce any adjacent passageway wall, and when the tube is rotated in the opposite direction, the tip is retracted back into the opening.

* * * * *